(12) United States Patent
Ambartsoumian

(10) Patent No.: US 7,350,703 B2
(45) Date of Patent: Apr. 1, 2008

(54) LOW TEMPERATURE RADIO FREQUENCY IDENTIFICATION TRACKING SYSTEM

(76) Inventor: Gougen Ambartsoumian, 1315 Fletcher Street, Laval, Quebec (CA) H7W 3Y3

(*) Notice: Subject to any disclaimer, the term of this patent is extended or adjusted under 35 U.S.C. 154(b) by 270 days.

(21) Appl. No.: 11/113,960

(22) Filed: Apr. 25, 2005

(65) Prior Publication Data

US 2005/0247782 A1  Nov. 10, 2005

Related U.S. Application Data

(60) Provisional application No. 60/564,604, filed on Apr. 23, 2004.

(51) Int. Cl.
*G06F 17/60* (2006.01)

(52) U.S. Cl. .................. 235/385; 235/462.13

(58) Field of Classification Search ............... 235/385, 235/380, 462.13, 462.46, 472.02
See application file for complete search history.

(56) References Cited

U.S. PATENT DOCUMENTS

| | | | |
|---|---|---|---|
| 4,694,283 A | 9/1987 | Reeb | |
| 5,583,819 A * | 12/1996 | Roesner et al. | 340/10.51 |
| 5,836,618 A | 11/1998 | Perlman | |
| 6,147,662 A | 11/2000 | Grabau et al. | |
| 6,294,999 B1 * | 9/2001 | Yarin et al. | 340/573.1 |
| 6,375,780 B1 | 4/2002 | Tuttle et al. | |
| 6,407,669 B1 | 6/2002 | Brown et al. | |
| 6,451,154 B1 | 9/2002 | Grabau et al. | |
| 6,836,215 B1 | 12/2004 | Laurash et al. | |
| 6,982,640 B2 * | 1/2006 | Lindsay et al. | 340/540 |
| 7,009,517 B2 * | 3/2006 | Wood | 340/572.1 |
| 7,091,864 B2 * | 8/2006 | Veitch et al. | 340/572.8 |
| 2004/0100415 A1 | 5/2004 | Veitch et al. | |
| 2005/0019213 A1 * | 1/2005 | Kechagia et al. | 422/57 |
| 2005/0024287 A1 * | 2/2005 | Jo et al. | 343/822 |
| 2006/0099567 A1 * | 5/2006 | Muller-Cohn et al. | 435/1.1 |

\* cited by examiner

*Primary Examiner*—Daniel Stcyr
(74) *Attorney, Agent, or Firm*—Michael Morency; James F. Ewing; Foley & Lardner LLP

(57) ABSTRACT

The present invention relates to a storage device comprising an antenna for transmission of data to and/or from a radio frequency identification (RFID) tag. More specifically, the invention relates to a low or ultra-low temperature storage device comprising an antenna for transmission of data between a radio frequency identification (RFID) tag and an RFID tag transceiver and its use for item identification, organization, classification, databasing, tracking or locating.

2 Claims, 1 Drawing Sheet

LOW TEMPERATURE RADIO FREQUENCY IDENTIFICATION TRACKING SYSTEM

CROSS-REFERENCE TO RELATED APPLICATIONS

This application claims priority on U.S. provisional application Ser. No. 60/564,604 filed Apr. 23, 2004, the entire content of which is hereby incorporated by reference.

BACKGROUND OF THE INVENTION (a) Field of the Invention

This invention relates to a storage device comprising an antenna for transmission of data to and/or from a radio frequency identification (RFID) tag. More specifically, the invention relates to the use of a storage device comprising an antenna for transmission of data to and/or from an RFID tag for item identification, classification, organization, databasing, tracking or locating.

(b) Description of Prior Art

It is routine practice in laboratory and/or industrial settings to store items in low temperature or cryogenic environments for the purpose of better preservation for short-term or long-term periods of time. Biotechnology and biomedical laboratories, for example, often store cell lines, DNA libraries, tissues, viral, bacterial, fungal and other biological specimens and biochemical agents in cryogenic environments for the purpose of better preservation for up to 15-20 years or more. Proper and secure labelling and identification of containers and items carrying these type of biological substances is pivotal for daily research, clinical and industrial operations.

Presently, item identification done by a handheld RFID reading device requires that a person searching in a storage device lift, for example, boxes or racks of boxes with one hand and hold the RFID reader in the other hand. In certain situations, for example, there might be hundreds or thousands of vials and/or containers stored in a single freezer or in a large liquid-nitrogen tank. Rapid identification of the right container or vial using the current labelling techniques is often difficult and time-consuming. Extended removal of a sample from a cold storage can be detrimental to the sample. For example, handling of cryogenic storage containers such as cryogenic boxes which are holding large number of cryogenic vials, micro-centrifuge tubes or microscope slides at room temperature, while seeking for the right vial or slide, can cause in many cases irreversible damage to the specimens contained therein and can decrease the viability and/or activity of cell cultures or other biological and/or biochemical substances. In addition, in cases of liquid nitrogen tanks, some spilling of the liquid nitrogen may happen which makes the procedure very inconvenient and even hazardous. If the RFID antenna and/or reader, individually or as a combined unit, is installed for example at an entry port or inside the device, the RFID tag can be read automatically during the lifting process and the person has both hands free to carry out the necessary operations such as entering or retrieving items from the low or ultra-low temperature storage device, or manipulating or moving items currently being stored.

It is also inconvenient and in some cases difficult or not practical to carry an RFID reader every time one needs to add, remove or move an item in a storage device.

Radio frequency identification (RFID) technology is an automatic way to collect product, place, time or transaction data quickly and easily without human intervention or error. An RFID tag can be programmed with information about a particular item and can be as small or smaller than a grain of sand.

It would be highly desirable to be provided with a storage device comprising an antenna for transmission of data to and/or from a radio frequency identification (RFID) tag and an RFID tag transceiver, wherein the antenna is installed on or near the storage device.

It would be highly desirable to be provided with the use of a storage device comprising an antenna for transmission of data to and/or from an RFID tag and an RFID tag transceiver for item identification, organization, tracking and locating.

It would be highly desirable to be provided with a storage device comprising an antenna for transmission of data between a plurality of RFID tags and an RFID reader(s) simultaneously for item identification, classification, organization, databasing, tracking and locating.

SUMMARY OF THE INVENTION

One aim of the present invention is to provide a storage device comprising an antenna for receiving data from or sending data to a radio frequency identification (RFID) tag wherein the antenna is installed on or near the storage device.

Another aim of the present invention is to provide the use of a storage device comprising an antenna, for receiving data from or sending data to an RFID tag, for item identification, classification, organization, databasing, tracking and locating.

It is another aim of the present invention to facilitate the identification and tracking of containers, specimens and samples in biomedical, biotechnology, industrial and related fields via employment of an RFID interrogation system.

Surprisingly and in accordance with the present invention, it has been discovered that the build up of ice, moisture, multiple ultra-low temperature freeze-thaw cycles and other environmental conditions such as storage at ultra-low temperatures ($-70°$ C. and below) or submersion in liquid nitrogen do not prevent identification or reading of RFID tags with a RFID reading device, nor does it prevent the programming of RFID tags. RFID tags with operating ranges as low as $-40°$ C. are known in the prior art (see for example, the Omron Electromagnetic Inductive RFID Data Carrier, Catalog number V600-D23P55). However, the use of RFID technology at ultra-low temperatures as described in the present invention have not been reported. It is well known in the scientific art that ultra-low temperature can cause stress related failure of a technology. Thus, it was a surprising discovery that RFID tags could withstand ultra-low temperatures and still be detected by an RFID antenna and read by an RFID reader.

One aim of the present invention is to provide a storage device comprising an antenna for transmission of data to and/or from a radio frequency identification (RFID) tag.

Another aim of the present invention is to provide the use of a storage device comprising an antenna for transmission of data to and/or from an RFID tag for item identification, classification, organization, databasing, tracking or locating.

In accordance with an embodiment of the present invention there is provided a low or ultra-low temperature storage device comprising an antenna for transmission of data between a radio frequency identification (RFID) tag and an RFID tag transceiver, wherein the storage device further comprises a door or port to access inside the storage device.

In a preferred embodiment of the present invention, the storage device further comprises a transceiver for data acquisition and communication between the RFID tag and the antenna.

In a preferred embodiment of the present invention, the antenna is located distal to the door or port of the storage device within a distance from the RFID tag to allow the antenna to transmit data between the RFID tag and the transceiver.

In a preferred embodiment of the present invention, the antenna is installed on or in an exterior surface, an interior surface, a door frame, a door, a hinge, a shelf, a rack, a drawer, a container, a seal, a compartment, an access port cover or an access port frame.

In a preferred embodiment of the present invention, the storage device is a refrigerator, a cold room, a refrigerated truck, a freezer, a cryogenic freezer, a dry ice container, or a cryogenic storage tank, and more preferably a liquid nitrogen storage tank.

In a preferred embodiment of the present invention, the low temperature is +4° C. and below.

In a preferred embodiment of the present invention, the ultra-low temperature is −70° C. and below.

In a preferred embodiment of the present invention, the ultra-low temperature is generated by liquid phase or vapour phase liquid nitrogen.

In a preferred embodiment of the present invention, the RFID tag is an active or passive RFID tag.

In a preferred embodiment of the present invention, the RFID tag is a read-only, write-once-read-many (WORM), or read-write RFID tag.

In a preferred embodiment of the present invention, the RFID tag operates in a high, intermediate or low frequency band.

In a preferred embodiment of the present invention, the high frequency band is between 850-950 MHz or 2.4-6.8 GHz, the intermediate frequency band is between 10-15 MHz, and the low frequency band is between 100-500 kHz.

In a preferred embodiment of the present invention, the RFID tag operates at a frequency band greater than or equal to 30 kHz.

In a preferred embodiment of the present invention, the data is variable information selected from the group consisting of content and characteristics of storage device and items, categories and subcategories that items and item content belong to, location of the storage device, position and coordinates of the item in the storage device, item, destination of the item, modification date, expiry date, date and time item was stored in, removed from or moved within the storage device, name of person storing item in, removing item from, manipulating item in, or moving item within the storage device, tracking number, identification number, patient name or ID number, place, origin, chronology and history of item or item content or item content creation, treatments and modifications that an item content or item content source or item content host were subjected to, contact coordinates, references and information on owner, distributor or supplier, description of content, instructions, name of mutation, type of mutation, category of mutation, name of disease, type of disease, category of disease, tumor name, any pathological condition, name of species, name of organism, name of organ, name of body part, name of tissue, and name of cell.

In accordance with another embodiment of the present invention there is provided a method of identifying, tracking or locating an RFID tagged item in a storage device according to the present invention, comprising activating the RFID tag; receiving data from the RFID tag by the antenna; and identifying, tracking or locating the item based on the data received.

In a preferred embodiment of the present invention, the antenna receives data from a plurality of RFID tags simulataneously.

In a preferred embodiment of the present invention, the antenna receives data from up to and including 150 RFID tags simultaneously.

In a preferred embodiment of the present invention, the storage device comprises a plurality of antennae.

In a preferred embodiment of the present invention, the storage device further comprises a plurality of transceivers for data acquisition and communication between the RFID tags and the antennae.

In accordance with another embodiment of the present invention there is provided a method of determining variable information for an item comprising an RFID tag kept at a low or ultra-low temperature, comprising: (a) providing a low or ultra-low temperature storage device as set forth in claim 1; (b) programming the RFID tag with variable information whenever the item remains in, is put into, removed from or moved within the storage device; (c) reading the variable information so programmed; and (d) determining the variable information for the item based thereon.

In a preferred embodiment of the present invention, the variable information is selected from the group consisting of content and characteristics of storage device and items, categories and subcategories that items and item content belong to, location of the storage device, position and coordinates of the item in the storage device, item, destination of the item, modification date, expiry date, date and time item was stored in, removed from or moved within the storage device, name of person storing item in, removing item from, manipulating item in, or moving item within the storage device, tracking number, identification number, patient name or ID number, place, origin, chronology and history of item or item content or item content creation, treatments and modifications that an item content or item content source or item content host were subjected to, contact coordinates, references and information on owner, distributor or supplier, description of content, instructions, name of mutation, type of mutation, category of mutation, name of disease, type of disease, category of disease, tumor name, any pathological condition, name of species, name of organism, name of organ, name of body part, name of tissue, and name of cell.

In a preferred embodiment of the present invention, the device allows determination of variable information for a plurality of items simultaneously.

In a preferred embodiment of the present invention, the device allows determination of variable information for up to 150 items simultaneously.

In a preferred embodiment of the present invention, the data is used to generate an inventory, database or classification of items.

In a preferred embodiment of the present invention, the data is used to identify, track the movement of or determine the location of an item.

In a preferred embodiment of the present invention, the variable information for the item is provided in real-time.

In accordance with another embodiment of the present invention there is provided a kit comprising: (a) a storage system for low or ultra-low temperature storage; and (b) an antenna for transmission of data between a radio frequency identification (RFID) tag and an RFID tag transceiver.

In a preferred embodiment of the present invention, the kit further comprises a transceiver for data acquisition and communication between the RFID tag and the antenna.

In accordance with another embodiment of the present invention there is provided a kit comprising: (a) an antenna for transmission of data between a radio frequency identification (RFID) tag and an RFID tag transceiver in a low or ultra-low temperature environment; and (b) a transceiver for data acquisition and communication between the RFID tag and the antenna.

In accordance with another embodiment of the present invention there is provided an information system for identifying, tracking or locating an item, comprising a plurality of storage devices according to claim 1, linked in a network, and means for linking the storage devices into the network, wherein linking the network allows for combining data comprising the variable information of each item in each storage device into a single list, for centralized access or searching thereof, wherein combining the data allows for identifying, tracking or locating an item stored within the plurality of storage devices.

For the purpose of the present invention the following terms are defined below.

The term "RFID interrogation system" is intended to mean at least one of the following: an RFID antenna, an RFID reader, an RFID integrated antenna/reader, or a device, a computer and/or a network of devices and computers that can do at least one of the following: sense, detect and/or register an RFID tag, transmit a signal acquired from any RFID tag, and receive, collect, store, manipulate, or process any information from an RFID tag.

The term "RFID antenna" is intended to mean an antenna or other device that is capable of sensing, registering, and/or detecting an RFID tag. Such an antenna can be of any configuration and can for example be simply a fragment of a coaxial or other cable or wire.

The term "low temperature" is intended to mean a temperature used for cold storage of an item, such as a biological or clinical specimen or chemical. Such temperatures include those which can be obtainable with, but not limited to, refrigerators and cold rooms (+4° C. and below) and freezers (0° C. to approximately −70° C.).

The terms "ultra-low temperature" and/or "cryogenic temperature" are intended to mean a temperature used for cryogenic storage of an item, such as a biological or clinical specimen, or other item. Such temperatures include those which can be obtainable with (but not limited to) cryogenic freezers (as low as −70° C. and below), and those commonly obtained with dry ice (−78.5° C.), vapour phase liquid nitrogen (approximately −150° C.) and liquid phase liquid nitrogen (−196° C.). Temperatures lower than −196° C. are also included in this meaning, for example, liquid helium (−270° C.). The sample or specimen may be a (but is not limited to) nucleic acid (such as vectors, plasmids, DNA, cDNA, RNA, extracts thereof, libraries thereof, nucleotides, oligonucleotides, gene expression systems, kits and their components, DNA constructs), amino acid, peptide, protein, lipid, cell, cell component(s), cell extract, phage, virus, bacteria, fungus or other microorganism, antibody, vaccine, enzyme, coenzyme, restriction enzyme, hormone, inhibitor, toxin, reagent, or other biological, biochemical, pharmaceutical or chemical compound, bodily fluid (including urine, blood and its components), tissue, organ, body part and/or entire organism (for example a microorganism, insect, fish, bird, mammal, plant), as well as natural and/or synthetic and/or genetically modified or combination thereof commercially available or non-commercially available substance, sample, specimen, species or product. The item, sample or specimen may be aqueous, amorphous, solid or gaseous or any combination thereof and includes any item, sample or specimen intended for, derived from and/or processed in a laboratory and/or industrial setting. Such a laboratory setting include, but are not limited to, biological, biomedical, biochemical, pathological, cytological, toxicological, clinical, diagnostic, forensic, pharmaceutical, veterinary, and agricultural.

For the purpose of the present invention low temperature is preferably +4° C. and below, more preferably 0° C. and below, and even more preferably −20° C. to −70° C.

For the purpose of the present invention ultra-low temperature is preferably −70° C. and below, more preferably −150° C. and below, and even more preferably −196° C. and below.

The term "low temperature storage device" is intended to mean a storage device that is capable of generating and/or maintaining a low temperature and is storing and/or capable of storing an aqueous, amorphous, solid, or gaseous substance, or any combination thereof, including but not limited to, any agricultural, biological, biomedical, biochemical or chemical sample, specimen or substance or any industrial item, Examples of such low temperature storage devices include, but are not limited to, a refrigerator, freezer, a cold room and a refrigerated truck or other mobile unit. Such devices may be automated and/or robotic.

The term "ultra-low temperature storage device" is intended to mean a storage device that is capable of generating and/or maintaining ultra-low (cryogenic) temperatures and is storing and/or capable of storing an aqueous, amorphous, solid, or gaseous substance, or any combination thereof, including but not limited to, any agricultural, biological, biomedical, biochemical or chemical sample, specimen or substance or any industrial item. Examples of such ultra-low temperature storage devices include, but are not limited to a cryogenic freezer, a dry ice container, a liquid nitrogen storage tank, and a cryogenic storage tank. Such devices may be automated and/or robotic.

Such low-temperature and ultra-low temperature storage devices are commonly known and used in the art and are commercially available from a number of suppliers.

The term "container" is intended to mean a system for storage, including but not limited to a vial, for example a cryogenic storage vial or a fluid collection or storage vial, a tube, for example a microcentrifuge tube, a bottle, a flask, a straw, a goblet, a cane, a storage box, including a cryogenic storage box, a holding rack, a sample bag, a pouch, a plate, a film can and a film cassette.

The following types of containers are commonly used in laboratory and industrial environments:

1) Vials, tubes, bottles: These containers include both non-cryogenic and cryogenic storage vials, tubes, microcentrifuge tubes, ampules and bottles: In many cases biological specimens are stored in commercially available 1.0-2.0 ml (in some cases from 0.2 ml up to 6.0 ml) special polypropylene (or other thermoplastic) vials and microcentrifuge tubes. Cryogenic vials are screw-cap secure seal vials designed for applications in cryogenic temperatures (from −70° C. to −196° C. and below, in some cases as low as −212° C.). Centrifuge and microcentrifuge tubes having a friction-seal or screw cap lid and able withstand temperatures as low as or lower than −70° C. are also included in this category. All polypropylene, polyethylene, polystyrene (or other thermoplastic), plastic or glass centrifuge tubes, sample collection and other tubes, tubes containing commercially available and non-commercially available samples, specimens, products or other substances, and other containers (thermoplastic and glass vials, tubes and cryogenic ampules with a volume capacity between 0.2 ml and 100.0 ml) and bottles (thermoplastic and glass bottles up to 12 L in volume) which are able to withstand temperatures as low as 4° C. or below, preferably −70° C. and below, more preferably −150° C. and below and even more preferably −196° C. and below are also included in this category;

Removable and non-removable components and parts of a container (for example, caps, lids, cap inserts, color coders and inserts for straws, goblets, canes) which can be sold separately are also included in this category;

2) Storage boxes and holding racks: Vials, cryogenic vials, centrifuge and micro-centrifuge tubes and the like and microscope and microarray slides and the like are often placed in metal or plastic (polycarbonate or other), cardboard, chipboard, or polystyrene container boxes (Cryogenic Boxes) or in holding/storage racks for carrying multiple vials and slides (vials, for example, can be held in so called straws, goblets or canes, which are metal or plastic holders, such as Nalgene CryoCane™; in some cases the straws or canes or individual vials are protected by encasing and sealing them with thermoplastic, for example, polyethylene sleeves, such as Nalgene CryoSleve™ and Nunc CryoFlex tubing). Similarly, film (including, but not limited to, X-ray film, motion picture film, video film and audio film) is often stored in storage cans or cassettes and such cans and cassettes are also intended to be included in this category;

3) Sample bags and pouches: Sample bags and pouches made of aluminum, paper and/or thermoplastic materials including, but not limited to, polyethylene, polypropylene, polyester, vinyl or composite materials are used in various laboratory, medical, clinical and industrial settings for low-temperature and ultra-low temperature storage, for example for storing chemicals, blood, blood products, biological and body fluids and their components, tissue, such as whole leaves or plants, organs, body parts or entire organisms and sterile fluids such as saline and the like;

4) Slides (including, but not limited to, microscope slides, microarray slides, hybridization slides and disease test screening slides): In some cases of cytology and cytopathology a specimen fixed on a slide is required to be stored under low or ultra-low temperature conditions. In addition, it is common practice in the art to mount DNA and RNA libraries on glass, or other material, slides. Slides premounted with commercially available and/or non-commercially available samples, specimens or products are widely available from multiple sources. Such slides may be stored at low or ultra-low temperatures until needed; and 5) Plates and dishes: Plates (including, but not limited to, cell culture plates, microtiter plates, PCR plates and their versions and variations) which are made of or contain polystyrene, vinyl, polyvinyl or polypropylene and which have multiple wells (for example, from 2 to 96, 384 and others) and are holding or capable of holding samples (commercially available and/or non-commercially available sample, specimen or product), including, but not limited to, nucleic acids, nucleic acid libraries, cell cultures, clones and viruses, often require low or ultra-low temperature storage. Disposable and non-disposable dishes such as Petri dishes and the like are used mainly for bacteriological and mycological applications. Cell culture and tissue culture dishes, flasks and tubes are often stored at low or ultra-low temperature conditions.

Such containers are commonly known and used in the art and are commercially available from a number of suppliers (for example: VWR, Fisher and others). Containers may be sold as complete systems or as individual components, such as lids and vials and dividers. Such containers can be obtained empty or containing any item.

BRIEF DESCRIPTION OF THE DRAWINGS

Having thus generally described the nature of the invention, reference will now be made to the accompanying drawing, showing by way of illustration, preferred embodiment thereof and in which.

DETAILED DESCRIPTION OF THE INVENTION

Figure 1:
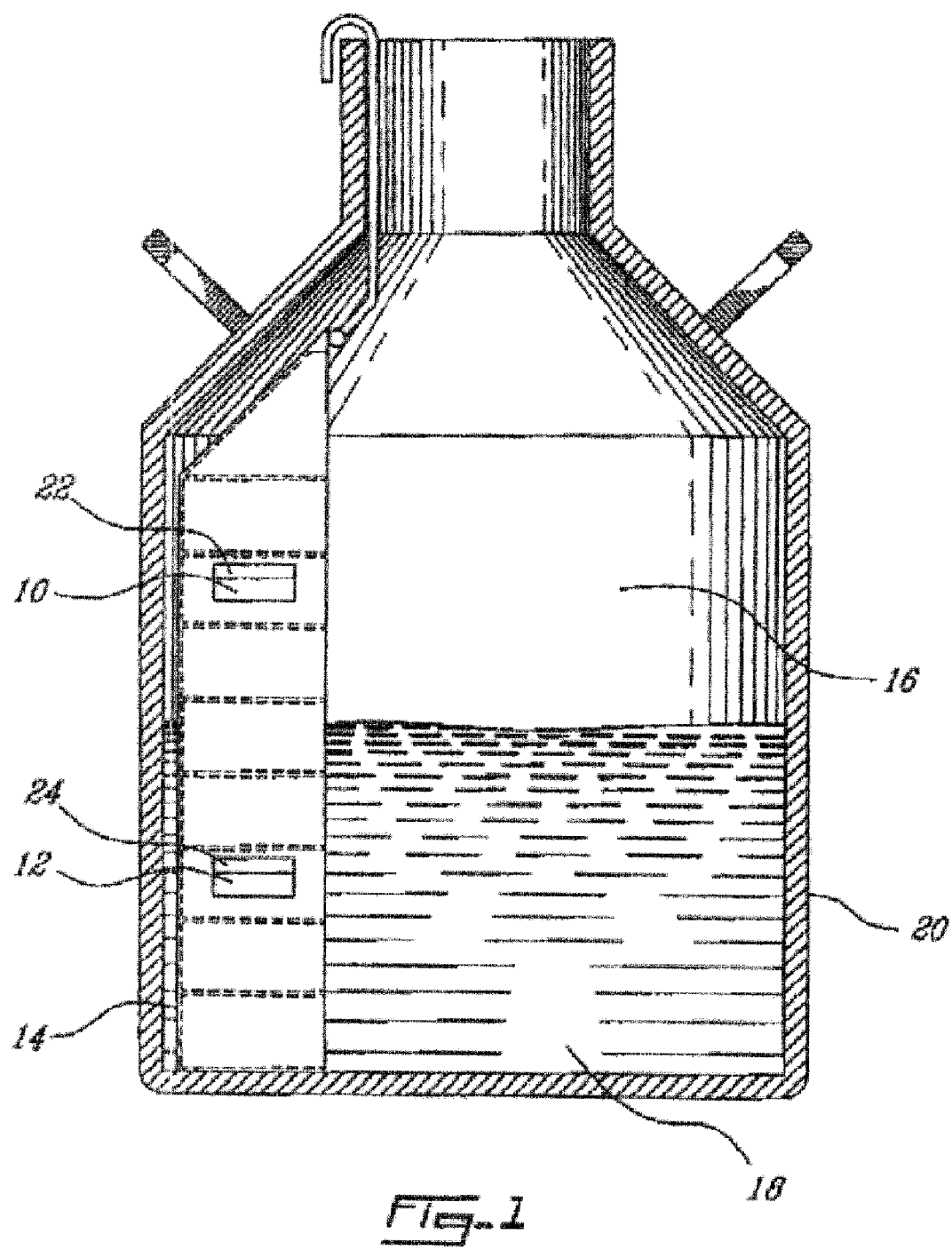
FIG. 1 is a schematic representation of a nitrogen tank containing an RFID labeled cryogenic boxed in liquid and vapour phase liquid nitrogen.

The present invention comprises an RFID antenna and/or an RFID reading device and/or an integrated RFID antenna—RFID reading device installed permanently or temporarily within, on or near a low temperature or ultra-low temperature storage device that can automatically sense and/or detect an RFID tagged item which is added to, removed from, stored in, or moved, manipulated or handled within the storage device. Individual RFID tagged items are sensed and/or detected or multiple RFID tagged items are sensed and/or detected simultaneously. This eliminates the need for carrying a RFID reader for each manipulation of an item. It also eliminates the problems related to locating a reader in a setting (for example, a laboratory) which might be misplaced, and in situations when there are multiple RFID readers, to locate the right one and then download the information from the RFID reader into a computer.

Radio frequency identification (RFID) technology is an automatic way to collect product, place, time or transaction data quickly and easily without human intervention or error.

The present invention is based partly on the surprising discovery of a new and useful application for Radio Frequency Identification (RFID) Technology, in ultra-low temperature (cryogenic) environments. An RFID system is a means of tagging an item where a label called a transponder, or RFID tag, comprises an electronic chip capable of communicating with a reader via a radio link. This allows the reader to receive the information stored in the RFID tag from a distance without any immediate or physical contact with the RFID tag or RFID tag carrying item.

An RFID system comprises a reader, or interrogator (a transceiver with decoder), its associated antenna and the transponder (Tag/RFID Card) that carries the data.

A reader typically contains a high frequency module (transmitter and receiver), a control unit and a coupling element to the transponder. In addition, many readers are fitted with an additional interface to enable it to forward the data received to another system, such as a computer or robot control system.

The reader transmits a low-power radio signal, through its antenna, that the tag receives via its own antenna to power an integrated circuit (chip). Using the energy it gets from the signal when it enters the radio field, the tag will briefly converse with the reader for verification and the exchange of data. Once that data is received by the reader it can be sent to a controlling computer for processing and management.

The antenna emits radio signals to activate the tag and read and write data to it. Antennas are the conduits between the tag and the transceiver, which controls the system's data acquisition and communication. Often the antenna is packaged with the transceiver and decoder to become a reader (a.k.a. interrogator), which can be configured either as a handheld or a fixed-mount device. In other instances the antenna is separate from the reader and can be located distal from the RFID reader. The antenna emits radio waves in ranges of anywhere from about one inch to 100 feet or more, depending upon its power output and the radio frequency used. When an RFID tag passes through the electromagnetic zone, it detects the reader's activation signal. The reader decodes the data encoded in the tag's integrated circuit (chip) and the data can be passed to a computer for processing.

RFID tags are categorized as either active or passive. Active RFID tags are powered by an internal battery and are typically read/write, i.e., tag data can be rewritten and/or modified. An active tag's memory size varies according to application requirements; some systems operate with up to 1 MB of memory. With the development of technology larger memory sizes will become available. The battery-supplied power of an active tag generally gives it a longer read range. The trade off is greater size, greater cost, and a limited operational life (which may yield a maximum of 10 years, depending upon operating temperatures and battery type).

Passive RFID tags operate without a separate external power source and obtain operating power generated from the reader. Passive tags are consequently much lighter than active tags, less expensive, and offer a virtually unlimited operational lifetime. The trade off is that they have shorter read ranges than active tags and require a higher-powered reader. Read-only tags are typically passive and are programmed with a unique set of data (usually 32 to 128 bits) that cannot be modified. Read-only tags most often operate as a license plate into a database, in the same way as linear barcodes reference a database containing modifiable product-specific information.

Although the passive type has a significant value in the present invention the active type has some important advantages for other applications in low temperature and ultra-low temperature environments and is encompassed by this invention.

RFID systems are also distinguished by their frequency ranges. Low-frequency (100 KHz to 500 KHz) systems have short reading ranges and lower system costs. They are most commonly used in inventory control and security access. Intermediate-frequency (10-15 MHz) systems have medium read ranges and are commonly used for access control. High-frequency (850 MHz to 950 MHz and 2.4 GHz to 5.8 GHz) systems, offering long read ranges (greater than 90 feet) and high reading speeds, are used for such applications as railroad car tracking and automated toll collection. Higher frequencies, like the 5.4 to 6.8 GHz band, are allocated for future use. The higher performance of high-frequency RFID systems incurs higher system costs. It should be noted, however, that frequencies are regulated by government legislations where different ranges of the electromagnetic spectrum are designated for different applications. There have not been established international standards and they therefore vary from country to country. The present invention is intended to operate at all operational frequency ranges, preferably a frequency greater than or equal to 30 kHz.

The significant advantage of all types of RFID systems is the noncontact, non-line-of-sight nature of the technology. Tags can be read through a variety of substances such as snow, fog, ice, paint, crusted grime, and other visually and environmentally challenging conditions, where barcodes or other optically read technologies would be useless. RFID tags can also be read in at remarkable speeds, in most cases responding in less than 100 milliseconds. The read/write capability of an RFID system is also a significant advantage in interactive applications such as work-in-process or maintenance tracking. RFID has become indispensable for a wide range of automated data collection and identification applications that would not be possible otherwise.

Both active and passive tags can be either read-only, write-once-read-many (WORM), or read-write, as outlined below:

Read-Only tags: tags which are pre-encoded with a unique serial number. It is possible to read it but the information cannot be modified or deleted;

Write-Once tags: tags on which it is possible to encode information once. This information can be read repeatedly without any possibility to modify or delete it; and Read & Write tags: tags on which it is possible to encode the memory partially or completely up to $10^5$ to $10^6$ times.

An encoding device for RFID writing (for example, an RFID read/write device, hand held computer, laptop or stationary computer, or a thermal transfer or other printing device that is also capable of RFID writing) can be independent and/or combined with and/or integrated in one or more storage systems as described above.

RFID tags come in a wide variety of shapes and sizes. For example, animal tracking tags, inserted beneath the skin, can be as small as a pencil lead in diameter and one-half inch in length. Tags can be screw-shaped to identify trees or wooden items, or credit-card shaped for use in access applications. The anti-theft hard plastic tags attached to merchandise in stores are RFID tags. In addition, heavy-duty 5- by 4- by 2-inch rectangular transponders used to track intermodal containers or heavy machinery, trucks, and railroad cars for maintenance and tracking applications are RFID tags. Other RFID tags are microchips half the size of a grain of sand.

One of skill in the art will thus realize that different types of RFID tags could be employed depending the specific set-up and application requirements.

New developments in RFID technology, anticollision protocol RFID tags, enhanced designs of RFID antennae and readers such as UHF long-range reader SARS MP9320 available from SAMSys Technologies and similar devices available from other suppliers, allow simultaneous reading of a large number of RFID tags (up to 150 at the present time). This feature can be used for automatic identification of multiple items for example in a laboratory environment where samples from patients are stored and/or manipulated in a low temperature or ultra-low temperature storage device in multiples, for example, a cryogenic box carrying 25-100 cryovials or a cryogenic tank rack can hold a number of cryoboxes at a time. In addition, identification, tracking and location of multiple storage containers containing for example multiple cell lines, viruses, DNA libraries, blood samples, tissue samples, commercial and/or non-commercial samples, specimens, products, containers and other items that are stored in an low temperature or ultra-low temperature storage device could be significantly facilitated by the application of RFID technology.

Due to rapid developments in technology the number of tags that could be simultaneously identified is growing and will continue to grow and therefore this invention is not limited to the number of RFID tags identifiable with the technology available at the present time and is intended to cover new developments in RFID technologies, including RFID antennae, tags, reader devices and/or accessories that might be developed in the future which will allow simultaneous identification of more RFID tags.

Due to wide variety of the items that could be stored in a laboratory, commercial and non-commercial settings this invention is not intended to be limited to the specific items mentioned and is intended to cover any item, object or product that could be stored in a low temperature or ultra-low temperature storage device.

The purpose of this invention is much broader than keeping simple inventory. Its purpose is to facilitate rapid identification, location and subsequent retrieval of items in a low temperature or ultra-low temperature storage device in a very dynamic environment for example in a diagnostic laboratory, in a hospital setting or in research laboratory where thousands or tens of thousands of items such as samples, microscope slides, cell lines, DNA and cellular and tissue banks are stored in multiple low temperature and ultra-low temperature storage devices, their compartments and containers. With the present invention, such information can be provided in real-time. Real-time information on important items is essential for efficient functioning of a laboratory or industrial setting.

The present invention relates to a low temperature or ultra-low temperature storage device that has an RFID antenna and/or reader built in, integrated into, installed on/in, added to, attached to, fixed on, linked to or associated with any stationary or removable parts or accessory of the storage device. The antenna can be integrated with the reading device or be separate from the reader. The antenna and the reader can be connected to each other through an electrical cord, wire or cable or via wireless connection. Multiple antennae and/or readers on a single storage device are also possible. The antenna automatically registers and keeps track of any item which is stored or put in, removed from or moved within the storage device.

In a cryogenic tank 20 for example and as illustrated in FIG. 1, an antenna may be built into, integrated in or installed around the main entry (opening) 24 of the tank. It may be built into, integrated in or installed on any internal or external, permanent or removable part of the tank or tank accessory which will allow automatic identification of an item stored or put into, removed from and/or moved within the cryogenic tank, A tank accessory can be for example a storage box 10, 12 with covers 22, 24 and/or rack 14. The boxes can be placed into different vertical positions inside a liquid nitrogen rack 14 to allow boxes to stay in the vapour phase 16 or to be inside the liquid phase of liquid nitrogen 18. The movement of an item is sensed by the antenna which transmits the signal to the reader and which registers the RFID labeled item. An RFID reader can be connected to another computer or a computer system and/or network which keeps track of all items and allows rapid identification, tracking and/or location of an item.

The storage device can be autonomous or integrated in and/or associated with a computer setting which can detect and/or keep track of any RFID tagged item.

Installation of an RFID antenna and/or reader on, around or inside an entry port and its surroundings or otherwise on, around or inside of a storage device will allow automatic registration of an RFID tag stored in, entering in, exiting from or moving within a storage device. Installation of an RFID antenna and/or reader inside a low temperature or ultra-low temperature storage device and/or in and/or on its various internal locations, components, accessories and/or compartments allows an even higher level of control. For example, an antenna and/or reader may be installed on an individual box, rack, shelf, drawer, compartment or a section of a freezer, cryogenic freezer, refrigerator etc., and which tracks an item inside the storage device when the item is moved from one location to another. This system is also useful for security purposes, where for example, removal of an item from a certain location triggers an alarm.

The present invention will help to eliminate human error and make the identification process more reliable and accurate. For example, when an RFID tagged item or multiple items to be stored in a storage device pass through an entry or exit port which includes an RFID antenna they are registered automatically whether they are located inside or outside of a box, bag, rack or in the hand of the person. The information is stored in the memory of a computer or other device that keeps an accurate log on the storage device number and location, item number and location inside the storage device, date, time and even the person who manipulated the item (for example, in instances where access to the storage device is limited by security access cards). Subsequently by entering the ID or any other parameter of the item it is easily identified, located and subsequently retrieved, as compared to the very laborious and time consuming exercise of manually searching for an item among hundreds or thousands of items stored in a single storage device or even worse, within multiple storage devices.

Using simultaneous reading of multiple RFID tags is a new and useful application that has many benefits for use in conjunction with low-temperature and ultra-low temperature storage devices. For example, in many cases the identification is done by a handheld RFID reading device and a person has to lift the item out of a liquid nitrogen tank by one hand and hold the reader in the other hand. In most cases some spilling of liquid nitrogen happens which makes the procedure very inconvenient and even hazardous. When the antenna and/or reader is installed at the entry port or inside the tank the RFID tag is being read automatically during the lifting process and the person has the other free hand to carry out other operations such as retrieving or manipulating the item. It is also inconvenient and in some cases difficult and not practical to carry an RFID reader every time an item has to be added to, removed from or moved within the storage device and/or needs to be identified. It might cause delays in the process of identification and in some cases create hazardous situations such as getting severe burns by liquid nitrogen or by ultra-low temperatures for the person who is trying to hold a rack in one hand and identify an item with a reader in the other hand.

The present invention offers the following benefits:

1) It saves money spent for replacement or repairs by significantly reducing the chances for a hand-held RFID reader to be damaged as a result of falling or some other cause due to its daily handlings and manipulations by personnel;

2) It saves time due to eliminating the need for locating a reader and eliminating the time required to go back to take it when the person forgot to bring it with him or her. In addition, it significantly reduces the time required for scanning of multiple RFID tagged items;

3) It facilitates the handling and manipulation of multiple items;

4) It increases the reliability and accuracy of identification since it will not depend on each person accurately detecting every item (for example, in some cases a person might forget to scan an item), but rather it is done automatically;

5) It eliminates human error and mix-ups such as reading an RFID tag by a handheld reader and storing it by mistake in a wrong storage device or entering the wrong information for its location;

6) It improves data management since each storage device can have its own profile which automatically detects every item entering, exiting, moved or stored in the storage device;

7) It significantly facilitates the tracking and locating of an item by using a log database;

8) It increases work safety by eliminating the need for a hand-held RFID reader and freeing at least one hand of a person to allow him/her to perform more important operations while the RFID reading is done automatically without human intervention; and 9) It increases security by using an internal RFID antenna/reader network connected to an alarm system which is triggered upon unauthorized removal and/or movement of an item from its location.

The antenna and/or reader can be installed on any internal and/or external surfaces of the storage device or within its proximity such that an RFID tag stored in, placed in, removed from or moved within can be read by an antenna. By this it is meant that the antenna and/or reader can be built in, integrated in, mounted on, linked to, associated with, and/or added to any permanent, removable or accessory part of the storage device including but not limited to an exterior surface of the storage device, an interior surface of the storage device, a door frame, a door, a seal (such as a rubber seal around an entry port or door frame) a hinge, a shelf, a rack, a drawer, a container, an access port cover, an access port frame. The storage device, its components or accessories can be manufactured with an antenna and/or reader integrated or an antenna and/or reader can be supplied as an accessory in the form of an independent unit or a kit that is integrated in, mounted on, linked to, associated with, and/or added to any permanent and/or removable part or accessory of a preexisting storage device.

The antenna and reader can be as a single unit, or they may be separated and communicate between a wire or by wireless technology.

The antenna can be of any configuration. It can be simply a fragment of a coaxial or other cable or a wire. It can be in the form of a gate through which a person must pass in order to gain access to the storage device, a loop of tubing for example surrounding a door frame or other access port or a flat surface such as a shelf or storage box. Antennae and antennae configurations are well known to those of skill in the art.

An RFID tag in connection with the present invention may be programmed with such variable information as selected from the group consisting of, but not limited to, content and characteristics of storage device and items, categories and subcategories that items and item content belong to, location of the storage device, position and coordinates of the item in the storage device, item, destination of the item, modification and expiry date, date and time item was stored in, removed from, manipulated in or moved within the storage device, name of person storing item in, removing item from, manipulating item in or moving item within the storage device, tracking number, identification number, patient name or ID number, place, origin, chronology and history of item or item content or item content creation, treatments and modifications that an item content or item content source or item content host were subjected to, contact coordinates, references and information on owner, distributor or supplier, description of content, instructions, name of mutation, type of mutation, category of mutation, name of disease, type of disease, category of disease, tumor name, any pathological condition, name of species, name of organism, name of organ, name of body part, name of tissue, and name of cell.

An RFID tag may be mounted on, embedded in, attached to or associated with an item to be stored in a low temperature or ultra-low temperature storage device. For example, an RFID tag may be adhered directly to the inside or outside of any removable or non-removable part of the item, for example a body side-wall, lid, lid insert, color coder, storage system insert, bottom or top of a container or microscope slide. In other cases the RFID tag may be simply placed into the item without adhesive. For example, an RFID tag may be placed into a vial or a well of a multi-well plate and kept within the vial or well by sealing the top. RFID tags may also be adhered to a protective sleeve which may be put over a container to encase and/or seal the container. RFID tags may be molded or embedded or manufactured into any permanent or removable part of a storage system, container or item as part of the manufacturing process.

An RFID tag may also be linked to an item through a cord, chain, strip or fragment of a material or any other method employed to link an RFID tag to an item.

An information system for identifying, tracking or locating an item stored in any of a number of different storage devices, which can be centrally located or located at different locations, can be generated by linking the storage devices in a network. The linking can be via wire or wireless connection. Regardless, linking the network allows for combining the variable information of each item in each storage device into a single list, for centralized access or searching thereof.

The present invention is not intended to be limited to any particular type of RFID tag, RFID encoding device or protocol, RFID antennae or RFID reading device, and covers all components of an RFID system that employ the concept(s) of RFID technology and its development in the future.

The teachings of all references cited herein are hereby incorporated by reference in their entirety.

The present invention will be more readily understood by referring to the following examples which are given to illustrate the invention rather than to limit its scope.

EXAMPLE I

RFID Functionality in Liquid and Vapour Phase Liquid Nitrogen

The present invention features the application of Radio Frequency Identification (RFID) transponder tags in cryogenic environments and their ability to be identified via a radio link reading device. Three individual RFID tags were placed inside each of two cryogenic boxes. The serial numbers of each RFID tag were read by the reader prior the experiment. The two boxes were placed into different vertical positions inside a liquid nitrogen rack to allow one of the boxes to stay in the vapour phase and the other one to be inside the liquid phase of liquid nitrogen. The rack was immersed into the liquid nitrogen tank for 10 minutes. Afterwards the rack was removed and immediately (within 5 seconds) the same serial numbers of the tags were read while the RFID tags were inside the closed cryogenic boxes. Next, the covers of the cryogenic boxes were opened and every individual tag was read directly. This confirmed the reading of the same serial numbers. The operation was completed within 30 seconds.

RFID tags may be read while still in such a liquid nitrogen container, i.e., without removing the boxes from the container.

The presence or absence of the plastic covers of the cryogenic boxes did not interfere with the readings of RFID tags in either box. Afterwards the same RFID tags in the same cryogenic boxes were immersed again into the same positions (vapour phase and liquid phase of liquid nitrogen) inside the liquid nitrogen tank for 72 hours. After 72 hours the cryogenic boxes were recovered and the experiment was repeated as described above. The exact same serial numbers were read without opening and after opening of the covers of the cryogenic boxes, indicating that the RFID system is completely functional at temperatures as low as at least −196° C.

EXAMPLE II

RFID Functionality at −80° C.

In another experiment the RFID transponder tags were applied to the sidewalls of three 50 ml polypropylene Falcon tubes. The serial numbers of the RFID tags were read with the RFID reader and the tubes were stored for 72 hours in a −80° C. cryogenic freezer. After 72 hours the doors of the freezer were opened and immediately (within 5 seconds) the same serial numbers of the RFID tags were read with the RFID reader. There was some slight build-up of ice over the RFID tags which had absolutely no interference with the readings.

RFID tags may be read while the door of such a freezer remains closed.

The tests were carried out by using a MINEC 13.56 MHz fully integrated RFID read/write hand-held terminal reader. Those skilled in the art, however, will recognize that this invention is not limited to the 13.56 MHz wavelength and any wavelength equal to or greater than 0.03 MHz is encompassed under this invention.

EXAMPLE III

Multiple RFID Tag Identification in Liquid Nitrogen

Device description: A RFID external antenna was installed beside the entrance port of a cryogenic liquid nitrogen tank. The antenna was connected to an MP9210 13.56 MHz RFID reader (available from SAMSYS Technologies) which was connected to a laptop computer with software to register and manage the information from the reader.

Ten cryogenic storage vials were labeled with RFID transponder tags and put into a cryogenic storage box. The serial numbers of each RFID tag were scanned individually prior placing them into the cryogenic storage box and closing the cover. The closed cryogenic box was passed at a distance of approximately 2-30 cm from a RFID antenna. All 10 serial numbers were registered and corresponded to the serial numbers which were obtained at the individual scan. The cryogenic box with the RFID tagged vials was put into a rack and immersed into liquid nitrogen. After 15 minutes the cryogenic box was retrieved and scanned with the RFID antenna. All 10 RFID tags were registered with serials numbers corresponding to the original readings.

EXAMPLE IV

Multiple RFID Tag Identification in Liquid and Vapour phase Liquid Nitrogen

Within the same setting as Example III, 10 cryogenic storage vials were labeled with RFID transponder tags. The serial numbers of each RFID tag were scanned individually at room temperature prior placing into the cryogenic storage box. Five RFID tagged vials were placed into each of two cryogenic boxes and the box covers were placed on. The closed cryogenic boxes were scanned with RFID antenna and the same serial numbers were registered. One of the boxes was placed in the top position and the other one in the lowest position of the rack to allow one of them to stay in liquid phase (lowest position) and the other one in vapour phase (top position) of liquid nitrogen. The rack was immersed into the liquid nitrogen tank. After 30 minutes the boxes were retrieved and passed in front of the RFID antenna immediately (within 5 seconds) after removal. The same serial numbers were read.

Subsequently, the same RFID tags in the same cryogenic boxes were immersed again into the same positions (vapour phase and liquid phase of liquid nitrogen) inside the liquid nitrogen tank. After 7 days the cryogenic boxes were recovered and the experiment was repeated as described above. The exact same serial numbers were read without opening of the covers of the cryogenic boxes.

The Examples III and IV indicate that multiple RFID tags can be registered and identified by a RFID antenna and reader at temperatures as low as at least −196° C.

EXAMPLE V

Multiple RFID Tag Identification at −80° C.

Device description: A RFID external antenna was installed beside the entry door of a −80° C. freezer. The antenna was connected to an MP9210 13.56 MHz RFID reader (available from SAMSYS Technologies) which was connected to a laptop computer with software to register and manage the information from the reader.

RFID transponder tags were applied to the sidewalls of five 50 ml polypropylene Falcon™ tubes. The serial numbers of individual RFID tags were read with the RFID reader and the tubes were placed into a Styrofoam rack. The rack was passed in front of the antenna at room temperature and all five serial numbers were registered in the computer. Afterwards the rack was stored at −80° C. in a cryogenic freezer. After 1 hour the freezer door was opened and immediately the rack was passed in front of the RFID antenna. The same serial numbers were registered by RFID reader. Afterwards the same rack with RFID labeled tubes was placed again inside the −80° C. freezer. After 7 days the rack was recovered and the experiment was repeated as described above. The exact same serial numbers were read without removing tubes from the rack.

Example V indicates that multiple RFID tags can be registered and identified by an RFID antenna and reader at temperatures as low as at least −80° C.

These experiments indicate that in liquid nitrogen as well as in an ultra-low temperature freezer the RFID system is functional and may be employed in cryogenic environments for identification and tracking purposes.

While the invention has been described in connection with specific embodiments thereof, it will be understood that it is capable of further modifications and this application is intended to cover any variations, uses, or adaptations of the invention following, in general, the principles of the invention and including such departures from the present disclosure as come within known or customary practice within the art to which the invention pertains and as may be applied to the essential features hereinbefore set forth, and as follows in the scope of the appended claims.

What is claimed is:

1. A low or ultra-low temperature storage device comprising an antenna for transmission of data between a radio frequency identification (RFID) tag and an RFID tag transceiver, the storage device having a door or port to access inside the storage device and an RFID reader installed at entry of said port, wherein the data is variable information selected from the group consisting of content and characteristics of storage device and items, categories and subcategories that items and item content belong to, location of the storage device, position and coordinates of the item in the storage device, item, destination of the item, modification date, expiry date, date and time item was stored in, removed from or moved within the storage device, name of person storing item in, removing item from, manipulating item in, or moving item within the storage device, tracking number, identification number, patient name or ID number, place, origin, chronology and history of item or item content or item content creation, treatments and modifications that an item content or item content source or item content host were subjected to, contact coordinates, references and information on owner distributor or supplier, description of content, instructions name of mutation, type of mutation, category of mutation, name of disease, type of disease, category of disease, tumor name, any pathological condition, name of species, name of organism, name of organ, name of body part, name of tissue, and name of cell.

2. A method of determining variable information for an item comprising an RFID tag kept at a low or ultra-low temperature, comprising:
   (a) providing a low or ultra-low temperature storage device comprising an antenna for transmission of data between a radio frequency identification (RFID) tag and an RFID tag transceiver wherein the storage device further comprises a port to access inside the storage device and an RFID reader installed at entry of said port;
   (b) programming the RFID tag with variable information whenever the item remains in, is put into, removed from or moved within the storage device;
   (c) reading the variable information so programmed; and
   (d) determining the variable information for the item based thereon;

wherein the variable information is selected from the group consisting of content and characteristics of storage device and items, categories and subcategories that items and item content belong to, location of the storage device, position and coordinates of the item in the storage device, item, destination of the item modification date, expiry date, date and time item was stored in, removed from or moved within the storage device, name of person storing item in, removing item from, manipulating item in, or moving item within the storage device, tracking number, identification number, patient name or ID number place origin, chronology and history of item or item content or item content creation, treatments and modifications that an item content or item content source or item content host were subjected to, contact coordinates references and information on owner, distributor or supplier, description of content, instructions, name of mutation, type of mutation, category of mutation, name of disease, type of disease, category of disease, tumor name, any pathological condition, name of species, name of organism, name of organ, name of body part, name of tissue, and name of cell.

* * * * *

UNITED STATES PATENT AND TRADEMARK OFFICE
CERTIFICATE OF CORRECTION

PATENT NO. : 7,350,703 B2  
APPLICATION NO. : 11/113960  
DATED : April 1, 2008  
INVENTOR(S) : Gourgen Ambartsoumian It is certified that error appears in the above-identified patent and that said Letters Patent is hereby corrected as shown below:

On the Title Page, Item (76)
Please correct the inventors name to read as follows:

-- Gourgen Ambartsoumian. --.

Col. 17, lines 1-27
Please correct Claim 1 to read as follows:

-- A low or ultra-low temperature storage device comprising an antenna for transmission of data between a radio frequency identification (RFID) tag and an RFID tag transceiver, the storage device having a door or port to access inside the storage device and an RFID reader installed at entry of said port, wherein the data is variable information selected from the group consisting of content and characteristics of storage device and items, categories and subcategories that items and item content belong to, location of the storage device, position and coordinates of the item in the storage device, item, destination of the item, modification date, expiry date, date and time item was stored in, removed from or moved within the storage device, name of person storing item in, removing item from, manipulating item in, or moving item within the storage device, tracking number, identification number, patient name or ID number, place, origin, chronology and history of item or item content or item content creation, treatments and modifications that an item content or item content source or item content host were subjected to, contact coordinates, references and information on owner, distributor or supplier, description of content, instructions, name of mutation, type of mutation, category of mutation, name of disease, type of disease, category of disease,

UNITED STATES PATENT AND TRADEMARK OFFICE
CERTIFICATE OF CORRECTION

| | |
|---|---|
| PATENT NO. | : 7,350,703 B2 |
| APPLICATION NO. | : 11/113960 |
| DATED | : April 1, 2008 |
| INVENTOR(S) | : Gourgen Ambartsoumian |

It is certified that error appears in the above-identified patent and that said Letters Patent is hereby corrected as shown below:

tumor name, any pathological condition, name of species, name of organism, name of organ, name of body part, name of tissue, and name of cell. --.

Col. 17 lines 28-33 & Col. 18 lines 1-31
Please correct Claim 2 to read as follows:

-- A method of determining variable information for an item comprising an RFID tag kept at a low or ultra-low temperature, comprising:

(a) providing a low or ultra-low temperature storage device comprising an antenna for transmission of data between a radio frequency identification (RFID) tag and an RFID tag transceiver, wherein the storage device further comprises a port to access inside the storage device and an RFID reader installed at entry of said port;

(b) programming the RFID tag with variable information whenever the item remains in, is put into, removed from or moved within the storage device;

(c) reading the variable information so programmed; and (d) determining the variable information for the item based thereon;

wherein the variable information is selected from the group consisting of content and characteristics of storage device and items, categories and subcategories that items and

UNITED STATES PATENT AND TRADEMARK OFFICE
CERTIFICATE OF CORRECTION

PATENT NO. : 7,350,703 B2
APPLICATION NO. : 11/113960
DATED : April 1, 2008
INVENTOR(S) : Gourgen Ambartsoumian It is certified that error appears in the above-identified patent and that said Letters Patent is hereby corrected as shown below:

item content belong to, location of the storage device, position and coordinates of the item in the storage device, item, destination of the item, modification date, expiry date, date and time item was stored in, removed from or moved within the storage device, name of person storing item in, removing item from, manipulating item in, or moving item within the storage device, tracking number, identification number, patient name or ID number, place, origin, chronology and history of item or item content or item content creation, treatments and modifications that an item content or item content source or item content host were subjected to, contact coordinates, references and information on owner, distributor or supplier, description of content, instructions, name of mutation, type of mutation, category of mutation, name of disease, type of disease, category of disease, tumor name, any pathological condition, name of species, name of organism, name of organ, name of body part, name of tissue, and name of cell. --.

Signed and Sealed this

Fifteenth Day of July, 2008

JON W. DUDAS
*Director of the United States Patent and Trademark Office*